United States Patent
Kuo

(10) Patent No.: US 6,960,170 B2
(45) Date of Patent: Nov. 1, 2005

(54) IMAGE PROCESSING SYSTEM FOR PREDICTING OVULATION

(76) Inventor: Youti Kuo, 88 Foxbourne Rd., Penfield, NY (US) 14526

( * ) Notice: Subject to any disclaimer, the term of this patent is extended or adjusted under 35 U.S.C. 154(b) by 38 days.

(21) Appl. No.: 10/237,204

(22) Filed: Sep. 9, 2002

(65) Prior Publication Data

US 2004/0049123 A1 Mar. 11, 2004

(51) Int. Cl.$^7$ .............................................. A61B 10/00
(52) U.S. Cl. ...................... 600/551; 382/128; 422/55; 422/68.1
(58) Field of Search ................................. 600/300, 551, 600/309, 573, 582, 584; 382/128, 130, 173, 194, 199, 204; 422/55, 58, 68.1, 69, 82.01, 82.02, 82.05, 82.09

(56) References Cited

U.S. PATENT DOCUMENTS

| | | | |
|---|---|---|---|
| 3,968,011 A | 7/1976 | Manautou et al. | |
| 4,385,125 A | 5/1983 | Preti et al. | |
| 4,770,186 A | 9/1988 | Regas et al. | |
| 4,815,835 A | 3/1989 | Corona | |
| 4,834,110 A | 5/1989 | Richard | |
| 5,572,370 A | 11/1996 | Cho | |
| 5,639,424 A | 6/1997 | Rausnitz | |
| 5,837,197 A * | 11/1998 | Porrazzo et al. | 422/61 |
| 5,914,271 A | 6/1999 | Law et al. | |
| 6,061,586 A | 5/2000 | Kuperman et al. | |
| 6,159,159 A | 12/2000 | Canter et al. | |
| 6,267,722 B1 * | 7/2001 | Anderson et al. | 600/300 |
| 6,364,844 B1 * | 4/2002 | Regas et al. | 600/551 |
| 6,582,377 B1 * | 6/2003 | Van Michaels et al. | 600/551 |
| 6,592,529 B2 * | 7/2003 | Marett | 600/551 |
| 6,623,698 B2 * | 9/2003 | Kuo | 422/68.1 |
| 6,735,803 B2 * | 5/2004 | Kuo | 15/22.1 |

FOREIGN PATENT DOCUMENTS

| | | | | |
|---|---|---|---|---|
| WO | WO 9528130 A1 * | 10/1995 | | A61B/10/00 |
| WO | WO 9847429 A1 * | 10/1998 | | A61B/10/00 |
| WO | WO 200106932 A1 * | 2/2001 | | A61B/00/00 |

OTHER PUBLICATIONS

Associated Press, "FDA Approves Saliva Test for Ovulation", Jan. 19, 2002.*
U.S. Appl. No. 10/059,477, filed Jan. 2002, Kuo et al.

* cited by examiner

Primary Examiner—Charles Marmor

(57) ABSTRACT

An image processing system for predicting ovulation using a test channel for collecting saliva sample and a miniature camera for capturing the image of the saliva at dried state for analyzing the crystalline patterns for ovulation prediction. A rotary bristle element is attached to the drive head and a notch-like test channel traverses the width of the drive head. A conductivity sensor is mounted on a wall of the test channel for detecting filling and drying of the saliva sample. An algorithm in the microprocessor analyzes the image of the dried saliva and calculates the characteristic line length of line segments of connected saliva dots. A ferning index is also defined and calculated based on the percentage of area coverage of line segments which are exceeding the threshold line length. Trend curves are established based on the daily saliva analysis in a woman's menstrual cycle for predicting days from the ovulation.

16 Claims, 15 Drawing Sheets

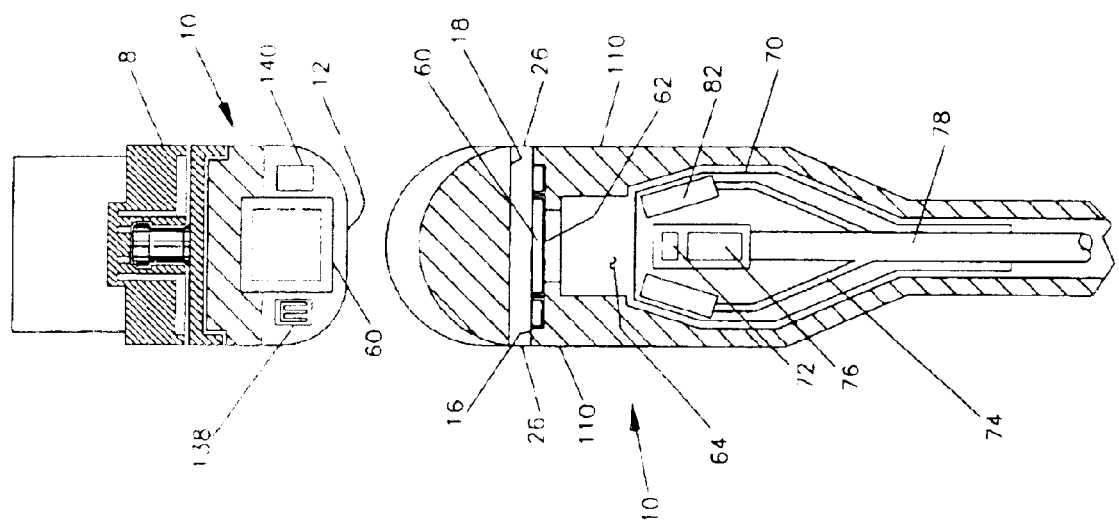

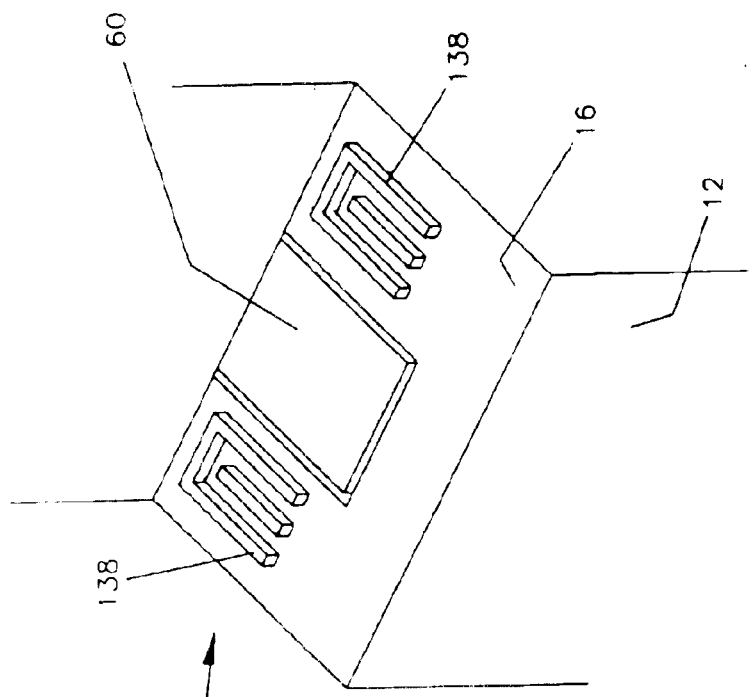
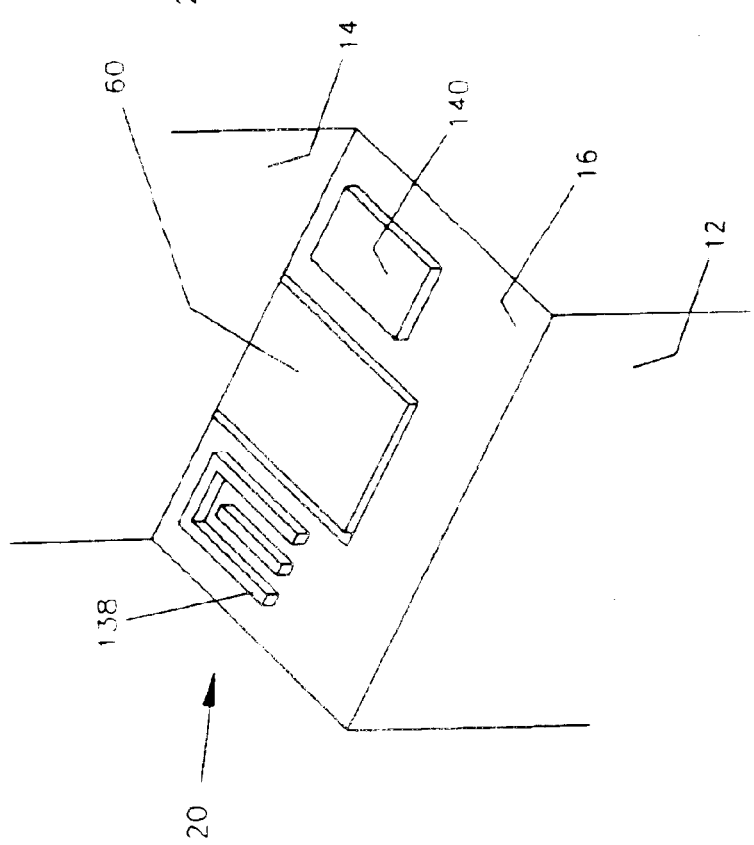
Fig 4a
Fig 4b

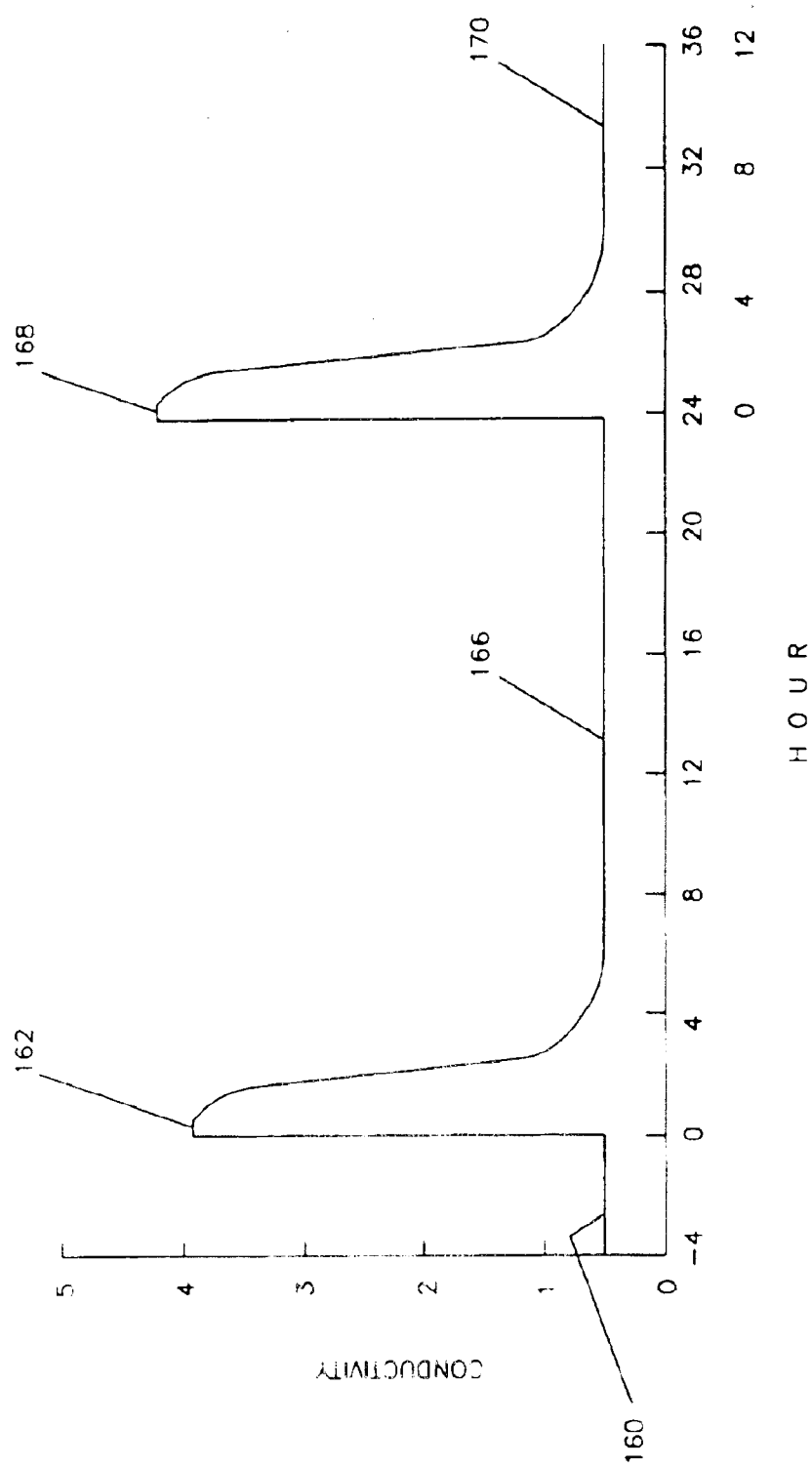

IMAGE PROCESSING SYSTEM FOR PREDICTING OVULATION

BACKGROUND OF THE INVENTION

There is a growing need for a home diagnostic system for monitoring various personal physiological conditions especially for the prediction of ovulation for women. A reliable method of predicting ovulation can determine a woman s fertility period for pregnancy as well as for birth control. A convenient oral device such as an electrical toothbrush having a built-in ovulation-monitoring capability is desirable for checking a woman's fertility condition on a daily basis.

(1) Field of the Invention

The present invention relates to ovulation-monitoring oral devices and electrical toothbrushes by detecting the crystallization and ferning pattern of dried saliva samples.

(2) Related Art

It is known that a woman's menstrual cycle, in general, lasts from 27 to 30 days, while menstruation lasts from 3 to 7 days in the cycle. In each cycle a woman can conceive only during about a three to six day window. As a woman's fertile period lasts about six days and ends on the day of ovulation a fertility test based upon detection of ovulation on the ovulation day is too late to be useful in determining the fertility time for planning. For advanced prediction a urine test on the concentration of luteinizing hormone (LH) can detect ovulation 1–2 days ahead of time but the test is not sufficient to detect the entire fertile period of three to six days.

There are many methods for predicting a woman's ovulation. It is known in the art to measure a woman's body temperature which increases with estrogen's rise to detect fertile times. It has been demonstrated that shortly after menstruation begins the body temperature decreases until ovulation starts, after that the temperature increases. During the menstruation period, the vaginal secretions also becomes increasingly viscous and to peak at the time of maximum fertility. These body temperature and viscosity measurements methods, however, are not reliable in determining fertile periods. Other ovulation prediction methods include a blood test and an urine test for detecting a surge in estrogen-related hormone. These tests can determine whether the woman is at ovulation instead of providing advanced signal of impending ovulation.

Saliva is a complex body fluid containing several different electrolytes including salts of sodium, potassium chloride and non-electrolyte components including several proteins, enzymes, and immunoglobulins. U.S. Pat. No. 4,770,186 by Regas et al. uses a sensor probe for measuring the electrical resistance of a saliva. Daily measurements are made beginning not more than five days following the beginning of menstruation. The onset of ovulation is determined as a function of a peak electrical resistance measurement following the onset of menstruation. A Stage A peak of salivary electrical resistance (SER) occurs approximately six days, plus or minus one day, prior to ovulation. After a sharp dip following the Stage A peak, Stage B peak occurs approximately 2 days before ovulation, plus or minus one day and it is a sign of imminent ovulation. Although the trend of changing electrical resistance of these electrolytes in saliva can be used to predict the impending ovulation, the appearance of multiple peaks prior to ovulation is too complicated to make a reliable judgement. Furthermore, the signal level of the electrical resistance is generally too weak to enable an accurate prediction.

Specifically, several patents in prior art describe various methods for collecting and diagnosing the contents of saliva for the prediction of ovulation. U.S. Pat. No. 3,968,011 by Manautou et al. shows the use of the optical density curves of saliva samples to indicate pregnancy. Such curves have a first peak and a smaller second peak in daily measurements; however, the second peak is eliminated when pregnancy occurs. In application, a paper test strip impregnated with a peroxidase and guaiac shows a color change when wet with saliva during the fertile period. The change is caused by the presence of peroxide in the saliva. The test strip is costly and may not be reused. U.S. Pat. No. 4,385,125 by Preti et al. monitors saliva for the concentration of certain long-chain alcohols, particularly dodecanol, for detecting ovulation. The dodecanol content of saliva remains at a relatively constant level throughout the menstrual cycle, but exhibits a single peak at the time of ovulation. Because the method requires the use of an incubated saliva sample, it is more suitable for laboratory tests than home use. Also the fact that the dodecanol level exhibits a single peak or spike precisely corresponding to ovulation does not enable prediction of a fertile period ahead of ovulation necessary for planning. U.S. Pat. No. 5,914,271 by Law et al. discloses that a saliva's calcium and magnesium concentration drops in the three to five day period immediately prior to ovulation. It provides methods of monitoring the calcium and magnesium concentration. All the methods include using a reagent composition such as calcium or magnesium sensitive dye or pigments which undergoes a visible change in the presence of a clinically significant threshold concentration of the ion. However, the use of reagent for a test stripe, ion-selective electrodes, or a handheld reflectometer for detecting different color shades is inconvenient for regular home testing.

Several commercially available hand held devices predict ovulation based on a measured peak in electrical resistance corresponding to sodium and potassium electrolyte levels which are reflective of hormone changes that occur several days before ovulation. The measured data on the changes of electrolytes in saliva may be inconsistent since an oral sensor probe is placed on the tongue where the thickness of the saliva layer may vary. While there are disadvantages associated with all of the above methods, each method demonstrates the feasibility of using an optical sensor or a conductivity sensor for measuring signals derived from a saliva sample to predict a fertile period or ovulation.

Another method for determining the ovulation is by visual examination of a woman's dried saliva. The method is based on observations of crystallized salt pattern in a dried saliva, which is referred as ferning pattern. The physical basis of ferning pattern is not well known. Some research results correlate the crystallization pattern with increases in the chloride content, changes in ionic strength and/or the content of sodium or potassium in the saliva. Research results mentioned in U.S. Pat. No. 4,815,835 by Corona indicates that saliva crystallization appears when the blood folliculin level has reached a certain height that coincides with the third or fourth day before ovulation. The crystallization pattern is visible under 100-fold magnification of a saliva sample on a slide. The crystallization lasts until 3 or 4 days after ovulation, when the presence of lutein inhibits the crystallization. At fertile times, microscopic viewing of dried saliva reveals a structure of salt distribution pattern that starts to form chains. This method of examination of saliva offers a reliable way to determine fertility.

U.S. Pat. No. 5,572,370 by Cho describes an apparatus for determining the fertile periods of women based on laboratory observations of crystallized saliva under high magnification. When a woman is most fertile, the saliva dries in fern-like patterns and during non-fertile periods the saliva pattern is random and generally appears as unconnected dots. When a combination of dots and fern-like patterns appear, it indicates that the woman is in a transitional period that a conception is possible but not highly likely. The patent states that laboratory tests have shown the fern-like structures appearing approximately three to four days prior to ovulation and ending two to three days after ovulation. However, the described method relies on the experience of visual observations and comparisons with standard patterns for determination of the fertile and non-fertile conditions of the woman being tested, therefore, it is subject to inaccuracies. Also described in U.S. Pat. No. 5,639,424 by Rausnitz is a portable fertility tester for viewing the ferning pattern of a dried saliva sample. The tester has a circular disc with transparent regions indexed to each of the days of the menstrual cycle for storing the saliva patterns for viewing. An ocular is provided with a magnifying lens for examining the appearance of a woman's saliva sample placed on the tester. After drying, a fern-like pattern indicates the woman at a fertile time or a structureless dotted pattern indicates non-fertile. The ovulation tester was approved by FDA in January of 2002 (The Associate Press news article on Jan. 19, 2002). The device, however, depends solely on qualitative viewing of multiple stored saliva samples for determining the fertility condition and no quantitative trend is established for more accurate prediction of ovulation.

Instead of qualitative visual observations of crystalline patterns, U.S. Pat. No. 6,159,159 by Canter et al. describes an approach of ovulation monitoring by quantitatively determining the degree of ferning on the basis of diffraction of light by a crystallized saliva sample. A laser light is directed onto a targeted location on a dried sample that reflects scattered light onto a two-dimensional photo diode array. The photo diode array inputs the light intensity profile to a microprocessor. The microprocessor has a programmed algorithm that calculates a local ferning index representing a characteristic structure in the diffraction pattern of the targeted location. By this means, a number of locations are selected for obtaining a summary ferning index that represents the degree of ferning of the whole saliva sample. The approach uses a threshold value for determining the fertility of the saliva sample. The accuracy of this method, however, depends on selected measurement locations, which may not represent the whole imaged area of a dried saliva.

The analysis of a ferning pattern requires image processing of a captured image of a dried saliva sample by a digital camera. The analysis involves the framing of line segments appearing in the imaged area of a dried saliva sample. A method of framing a test image for comparing with a template is described in U.S. application Ser. No. 10/059477 by Kuo et al. for signature verification and character recognition. With the input of the stored pixel values, an OCR program proceeds to frame a first test character by scanning from the left end of the field toward the right end of the field. The first test character frame increases in size in the direction where the coverage area of dark pixels increases. This operation is repeated until the final frame is reached, by which further increase of frame size in any direction does not increase the coverage area of dark pixels. The template character that presents the best match is identified as the character for the test character. The methodology as described is for determining the best match of images, however, it is not applicable for characterizing the structure of a crystallization pattern of a dried saliva sample.

For daily home measurement of the Ferning pattern of a dried and crystallized sample, a convenient and well defined saliva collection method needs to be developed. The prior art has disclosed various means for collecting saliva samples. U.S. Pat. No. 4,834,110 by Richard describes a suction cup for collecting a saliva sample. Suction is applied to a person's cheek around the parotid salivary duct and a pulsing pressure or electrical stimulation is applied to promote the flow of saliva to a collector vessel. The device is for one-time use in laboratory testing and it does not control the sample size for testing. Another device using a collecting cup for monitoring saliva is disclosed in U.S. Pat. No. 6,061,586 by Kuperman et al. The device includes a sample kit and an electrode assembly for immersion within a patient's saliva. The sample kit is comprised of a syringe-like element with a piston and a sponge member for absorbing the saliva which is to be compressed by the piston into the collecting cup. Disadvantages of the method are potential contamination of saliva by the sponge and the mechanical handling of the saliva that may impact the alignment of salts pattern.

A convenient saliva collection and testing method is disclosed in U.S. Pat. No. 6,623,698 by Kuo. It describes the use of a biosensor electrical toothbrush that has a drive head having a test channel and a renewable biosensor system within the test channel for performing routine saliva tests. The drive head stimulates saliva production and collects a fixed quantity of saliva in the test channel where measurement signals are produced by sensors. The signals are transmitted to a microprocessor in the handle for storage and diagnostic analysis of the saliva sample. The brush handle also includes a display means, a battery, a motor and a reservoir for storing a reagent which is supplied in controlled quantities to the channel during saliva testing. The biosensor electrical toothbrush as described, however, is for measuring properties of a liquid saliva. It is not for capturing an image of a dried saliva sample for detecting crystallization.

In summary, there have been a significant number of patents which utilize saliva samples to predict a woman's ovulation. While various patents in the prior art describe methods for predicting ovulation, none is capable of performing the stimulation and collection of saliva and testing the saliva sample in an all-in-one handheld device for economic, efficient and convenient repeated regular uses at home.

It is therefore an object of this invention to provide a portable handheld diagnostic oral device which stimulates saliva production and collects saliva samples in a test channel. It is another object of the invention to test dried saliva samples of a user for the purpose of monitoring the Ferning crystallization pattern on a daily basis. It is a further object of the invention to provide a portable hand held diagnostic device which has a toothbrush component.

SUMMARY OF INVENTION

A preferred embodiment of the oral device is configured as an ovulation-monitoring electrical toothbrush which has a handle and a brush head. The handle contains a battery, microprocessor, motor, a rotatable driveshaft, display and a miniature digital camera for storing an image of dried saliva sample. A plurality of bristles which rotate or oscillate are attached to the top of the drive head and a notch-like test channel traverses the width of the bottom of the drive head. A conductivity sensor is mounted on the walls of the test channel for detecting filling and drying of a saliva test sample. The camera captures and transmits an image of the dried saliva sample to the microprocessor. An algorithm in the microprocessor analyzes the saliva image and calculates a ferning index of a dried saliva sample taken daily in a woman's menstrual cycle for establishing a trend curve for predicting ovulation.

In operation, a switch is turned on to start the oscillation of the bristle elements. This also causes vibration of the drive head and the open test channel. When placed in contact with the tongue or cheek, the vibrating channel walls stimulate the secretion and accumulation of saliva under the tongue or elsewhere in the mouth. Saliva is drawn into the open channel by its capillary action, facilitated by a partial vacuum caused by the vibration of the channel walls. The complete filling of the test channel is detected by the sudden drop of the salivary electrical resistance measured by a conductivity sensor which is positioned at the inner most location of the open channel. The same sensor later detects the drying of the saliva as the electrical resistance across the electrodes increases due to the evaporation of the liquid saliva sample. After a predetermined drying time period, the camera captures the image picture of the dried saliva sample. A ferning index is computed based on the connectivity of dark pixels of saliva dots appearing in the dried saliva sample, whose image pattern is analyzed by a process of framing line segments of connected saliva dots and an algorithm that determines a characteristic line length of the saliva sample's crystallization pattern. The growths of the characteristic line length and the ferning index are plotted as trend curves and displayed in the display unit attached to the handle. Based on the trend curves a prediction of impending ovulation is provided.

The essential components of an ovulation-monitoring electrical toothbrush include; 1) a handle which serves as a housing for a motor and electrical components; 2) a replaceable bristle unit having a rotary bristle element; 3) a drive head having a driver component that imparts oscillation of the bristle element; 4) a test channel for containing a saliva sample; 5) a conductivity sensor for detecting filling and drying of saliva; 6) a camera for capturing an image of dried saliva sample; 7) a microprocessor having a control program for the operation of the device; 8) an image processing algorithm for computing the Ferning Index of a crystalline pattern; and 9) a display.

BRIEF DESCRIPTION OF THE DRAWINGS

FIG. 1a is a side cross-section view of a saliva-imaging (ovulation monitoring) electrical toothbrush.

FIG. 1b is an enlarged view of the drive head of FIG. 1a.

FIG. 2a is a back cross-section view of the saliva-imaging electrical toothbrush of FIG. 1a.

FIG. 2b is a top cross-section view of the saliva-imaging electrical toothbrush of FIG. 1a.

FIG. 4a is a prospective view of the lower wall of a test channel mounted with first and second sensors, and an optically transmissive window.

FIG. 4b is a prospective view of the lower wall of a test channel mounted with two conductivity sensors, and an optically transmissive window.

FIG. 4c is a plot of response of conductivity sensor indicating filling and drying of a test channel.

FIG. 13a is an ovulation-monitoring oral device with vibration test head.

FIG. 13b is an enlarged view of the test head of FIG. 13a.

FIG. 14a is an ovulation-monitoring oral device.

FIG. 14b is an enlarged view of the test head of FIG. 14a.

DETAILED DESCRIPTION OF THE INVENTION

Figure 1C:
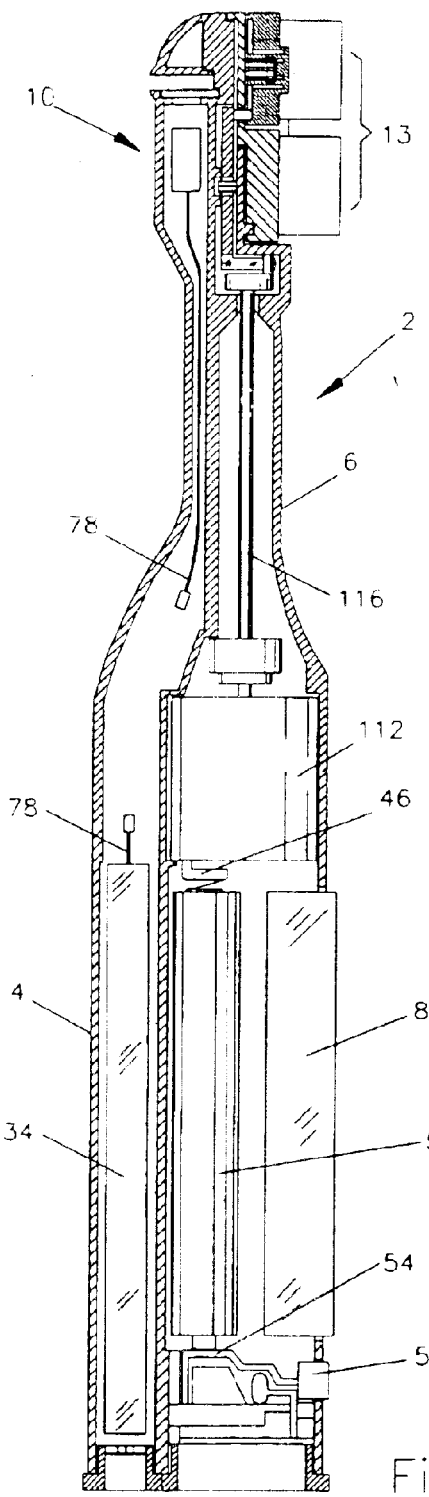
Figure 1B:
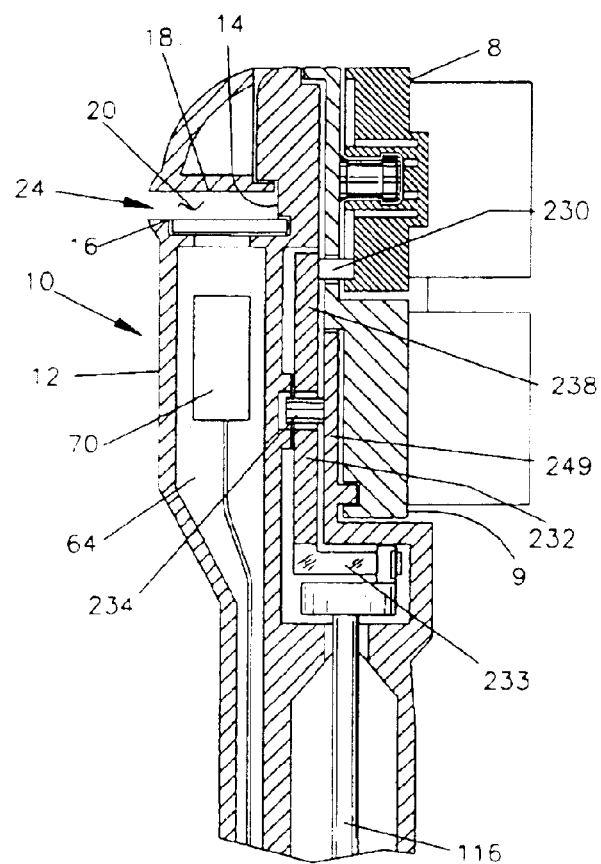

FIGS. 1a and 1b show an ovulation-monitoring electrical toothbrush 2 having a handle 4 and a drive head 10 connected by neck 6. Replaceable bristle unit 13 having rotary bristle element 8 and stationary bristle element 9 is detachably mounted on drive head 10. Motor 112, batteries 50, microprocessor 34 and display 80 are positioned in handle 4. Leaf spring contact 54 is situated at the end of battery 50 and switch 52 extends through an opening in the base of the handle. Batteries 50 are connected to motor 112 by contact 46. Drive shaft 116, having a central longitudinal axis with first end and second end, is positioned in neck 6. The replaceable bristle unit 13 is engaged with oscillation linkage 233 with straight lever 232 contained in drive head 10. Oscillation linkage 233 having straight lever 232 consists of swing arm 238 at the output end, notch walls 230 at the input end, bushing through hole positioned between the two ends for accommodating stud shaft 234 which extends from the underside of top wall 249 of drive head 10. With bushing hole engaged with stud shaft 234 which extends from the inner surface of top 249, straight lever 232 converts the rotation motion of drive shaft 116 to planar oscillation of swing arm 238. Since stationary bristle element 9 is used, output swing arm 238 of the linkage engages only with the drive, notch of the rotary bristle element 8 and causes it to have angular oscillation. A detailed description, of the drive mechanism of drive head 10 for the oscillation of the bristle element 8 is given in U.S. Pat. No. 6,735,803 by Kuo.

Also referring to FIGS. 2a and 2b, drive head 10 has side surface 110, bottom surface 12, and camera assembly 70 in cavity 64. Test channel 20 is recessed in bottom surface 12 and traverses the width of drive head 10. The test channel has a channel wall comprising an upper wall 18, a lower wall 16 as well as a base 14, all of which form a flow channel with front opening 24 which is opposed to base 14. Lower wall 16 has optically transmissive window platen 60 for enabling capturing the image of a saliva sample by camera assembly 70. Test channel 20 also has two side openings 26 which are opposed to each other on the side surfaces 110 of the drive head. The channel gap between the upper and the lower walls is defined by front opening 24 and side opening 26. It is optimally designed with a width narrow enough for inducing capillary flow and for holding saliva within the open channel but sufficiently wide to allow for the passage of cleaning water to flush out saliva inside the test channel. Vent groove (not shown) is situated along the length of the channel base 14. The width of the vent groove is sufficient to vent entrapped air during filling of the test channel with saliva but is too narrow for saliva or water to penetrate into the groove.

Figures 3A, 3C:
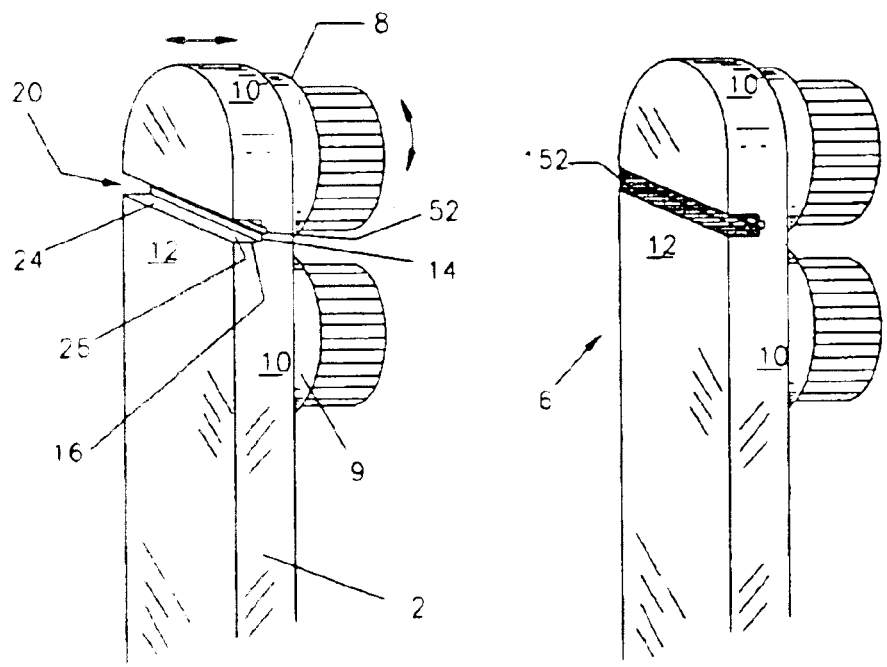
FIG. 3a is a prospective view of the toothbrush shown in FIG. 1a with empty test channel.
FIG. 3c is a prospective view of the toothbrush shown in FIG. 1a having a saliva sample in the test channel.
Figure 3B:
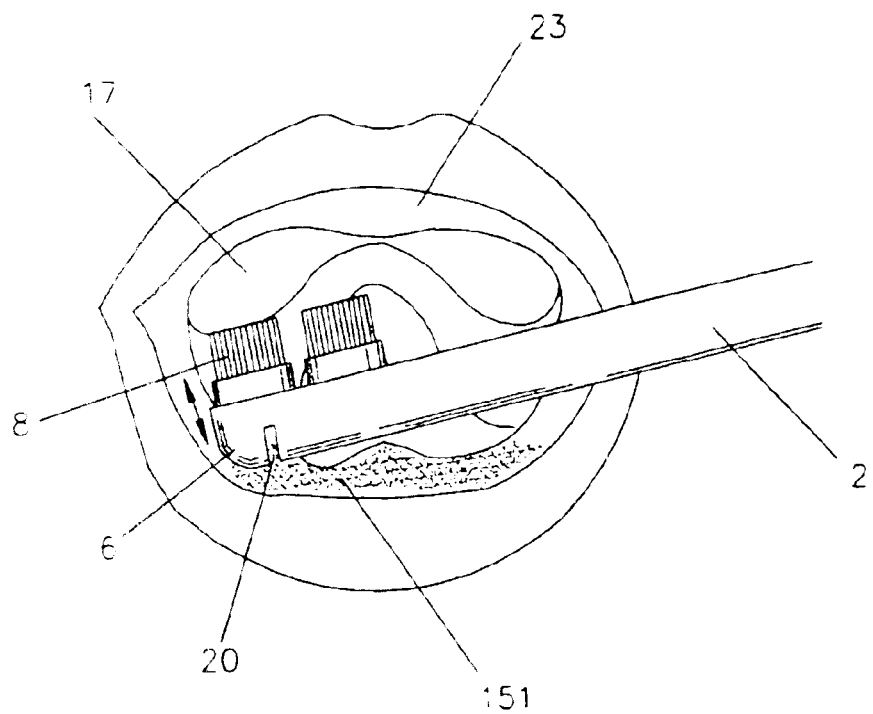
FIG. 3b is a side elevation view of the toothbrush shown in FIG. 1a positioned under the tongue of a user's mouth for saliva collection.

Vibration of the drive head stimulates production of saliva by the salivary glands. Biased disk 40 and off-centered rod 44, which are mounted on drive shaft 116, impart a vibrating motion to drive head 10. FIG. 3a shows the oscillation of two bristle elements and the vibration of the drive head. FIG. 3b shows the collection of saliva by drive head 10, which is placed in a mouth 23 under tongue 17 with the test channel 20 in contact with saliva pool 151. In operation, the vibration of the drive head generates a low pressure or partial vacuum condition in the vicinity of the test channel. When immersed in a pool of saliva, the low-pressure zone immediately next to the test channel induces saliva to flow into the test channel. The saliva flow pushes air out or forces entrapped air into vent groove (not shown) to release it from the test channel. After the vibration ceases, the drive head is removed from the saliva pool. The surface tension and the viscosity of the saliva retain saliva 152 inside the narrow test channel as shown in FIG. 3c. The gap across the channel is filled thereby forming continuous saliva medium for sensor measurement.

FIGS. 2a and 2b show back and top cross-section views respectively of the ovulation-monitoring electrical toothbrush shown in FIG. 1a. In a preferred embodiment, first sensor 138 and second sensor 140 are used in the test channel 20 in which first sensor 138 is a conductivity sensor. First sensor 138 is positioned on the lower wall 16 for measuring the salivary electrical resistance and conductivity corresponding to the empty state, filling of the test channel and the drying of a saliva test sample across the electrode and the counter electrode. FIGS. 4a and 4b show test channel 20 with the upper channel wall removed for indicating the mounting of the first conductivity sensor and the second sensor mounted on the lower wall 16 on each side of the window platen 60. The first conductivity sensor consists of a matrix of electrode and counter electrode The electrodes have a depth forming gaps for being immersed in the saliva pool. When the gaps are deprived of liquid saliva as the saliva sample is dried up, the conductivity sensor shows breakdown of the conductance across the electrode and the counter electrode. Filling of the test channel is automatically determined as the conductivity readings of the conductivity sensor start to exceed a predetermined threshold conductivity value which is indicative of the filling of the test channel. This threshold conductivity value is pre-determined at the condition that the electrode matrix is filled or wetted with a saliva sample. Changes of electrical signal may indicate filling or drying of the saliva sample in the electrode matrix and in the test channel. Optionally as shown in FIG. 4b second sensor 140 may be a moisture sensor for enhancing the detection of the drying of the saliva sample or it may be another type of sensor for measuring a property of the saliva sample for additional diagnosis. A combination of the readings of the first and the second sensors may be used for checking on the consistency of the states of filling of the test channel and the drying of the saliva sample. These sensors are connected to the microprocessor which has a signal processor for amplifying signals received from the sensors and filters as input to an A/D converter (not shown). The microprocessor has a random access memory (RAM) unit and a programmable read only memory (PROM) unit. The RAM unit contains programming related to the operation of the electrical components and the PROM contains algorithm software for sensor signal calibration and image processing. The information stored in RAM unit is read through an I/O. Furthermore, microprocessor 34 controls the vibration of the drive head, the activation of the first and the second sensors and the analysis of the output signal from the sensors. The sensors are activated at the same time as the drive head vibrates for monitoring the filling of the test channel by the inflow of saliva.

The function of the first conductivity sensor is further illustrated in FIG. 4c. First conductivity sensor 138 detects the moment of the filling of the test channel when the reading of electrical conductivity jumps from low flat level 160 of the empty state to reach high plateau level 162. Its input to microprocessor 34 activates an acoustic or visual signal for the user to remove upper channel wall 18 for exposing the saliva sample for drying Moreover, at the same time it triggers a timer (not shown) inside handle 4 in communication with microprocessor 34 that registers the start of a drying period. Also, the first sensor 138 is programmed to subsequently read the electrical conductivity of the saliva sample at a pre-determined time intervals, for example at every 30 minutes, while the saliva sample is undergoing a drying process. Following the sequence of repeated measurements of electrical resistance and conductivity across the gaps of the electrodes and when the decrease of conductivity reaches low plateau level 166, the conductivity sensor detects the drying of the saliva sample. At the absence of liquid saliva the gap between an electrode and a counter electrode is not filled, accordingly the conductivity measured by the first conductivity sensor is at the same level as that of the empty state 160 of the test channel. Optionally, a humidity sensor may be positioned as a second sensor 140 in communication with microprocessor 34 for confirming the dried state of the saliva sample. Following a predetermined time period at the plateau state of dried saliva sample, the control program of the microprocessor activates the camera assembly to capture the image of the dried saliva. For accelerating the drying process, a heating element may be mounted on lower wall 16 and the duration of heating may be controlled by the microprocessor or monitored by the first conductivity sensor or a humidity sensor for ensuring the drying of the saliva sample before triggering the camera assembly for capturing the image of the saliva sample for analysis. FIG. 4c also illustrates the detection of filling of the test channel and the drying of a saliva sample 24 hours after the preceding filling of the test channel. The new plateau 168 may vary from the preceding plateau 162 as the electrical resistance of a woman's saliva may change significantly as the day of measurement is close to the day of ovulation. However, the subsequent low level 170 is more consistent with low level 160 of empty test channel and low plateau 166 of the preceding dried saliva sample, which does not fill the gap between electrode and counter electrode. For the consistency of the sensor reading related to possible effects of saliva residue in the test channel and sensor signal drifts in the system, the conductivity sensor is automatically calibrated prior to the collection of a saliva sample. Alternatively, with the upper wall detached, a saliva sample can be placed directly on top of the transmissive window platen for drying and for image capturing by the camera assembly. This exposed test channel provides an open test platen configuration with the saliva collection means separated from the saliva testing handle device.

Figure 5C:
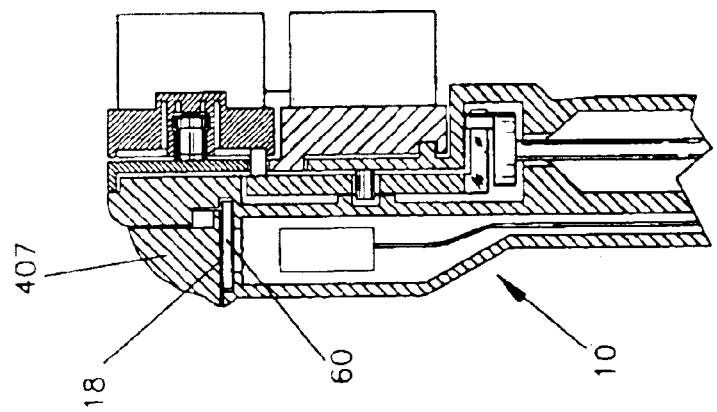
FIG. 5c is a cross-section view of a drive head with the detachable test channel wall at the closed position.
Figure 5B:
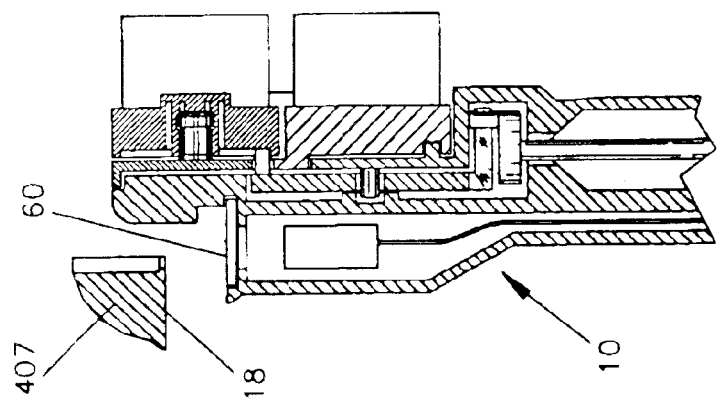
FIG. 5b is a cross-section view of a drive head with the detachable test channel wall removed.
Figure 5A:
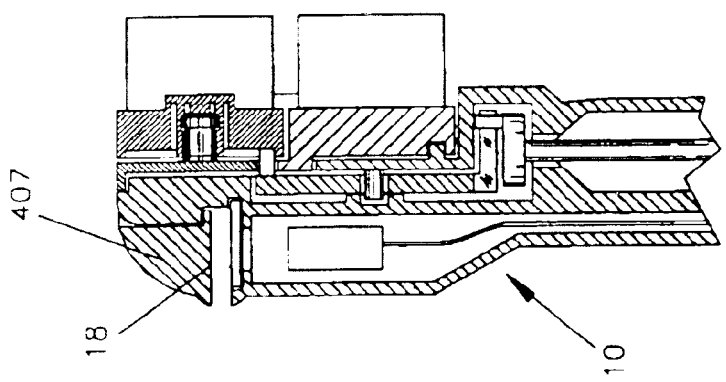
FIG. 5a is a cross-section view of a drive head with the detachable test channel wall at the open position.

After the image of a dried saliva sample is captured, the test channel may be cleaned for reuse for the next collection and testing of a saliva sample. Test channel 20 of the present invention is for repeated uses. In order to thoroughly clean the test channel 20 after each testing, upper wall 18 of the test channel is made detachable. FIG. 5a, which is a repeat of FIG. 1b, shows the mounting of a detachable upper wall assembly 407 having upper wall 18 at the open position with respect to the test channel 20, whose lower wall 16 is mounted with transmissive window platen 60, first sensor 138 and second sensor 140. FIG. 5b shows lower wall 16 of the test channel with upper wall assembly 407 detached for drying and cleaning purposes. When upper wall assembly 407 is detached, transmissive window platen 60, first and second sensors 138 and 140 are accessible for thorough cleaning. FIG. 5c shows the upper wall assembly 407 at the closed position. In application upper wall assembly 407 is attached to drive head 10 by any suitable self-locating, snap-on fastening mechanism. For preventing contamination of the test channel by the toothpaste, the test channel may be closed prior to brushing. Structually the upper channel wall may be equipped with a slidable sleeve mounted on the upper channel wall that can be pushed down from the open position to close the periphery of the test channel entrance for preventing contamination from the brushing action. Upon completion of the brushing action, then the slidable sleeve is pulled back to the open position. As a part of the upper channel wall, the slidable sleeve can be detached together with the upper channel wall from the drive head for facilitating the drying of the saliva sample. The concept and the design of a slidable sleeve for sealing a test channel of a saliva-monitoring toothbrush has been described in U.S. Pat. No. 6,623,698 by Kuo.

Referring again to FIGS. 1a and 1b, the drive head 10 contains a digital camera assembly 70 in cavity 64 situated below the transmissive window platen 60 of lower wall 16 of the test channel 20. Further shown in FIG. 2a, the camera assembly 70 has a charge coupled device (CCD) 76 having a two dimensional photosensor array, an optic assembly 72 for focusing on image area 62 on optically transmissive window platen 60 and an illumination assembly 74 providing targeted illumination to the image area 62. Camera assembly 70 is positioned so that it has the desired field of view and is focused on the image area 62 of the window platen 60 for transmitting signals representative of the image received from the image area to display system 80 by cable 78. In addition, FIG. 2b, which is a top view of test channel 20, shows that first connectivity sensor 138 and second sensor 140 are positioned on each side of the window platen 60 in the test channel 20. In application, the transmissive window platen may be of a glass or an optically transparent plastic material.

The illumination assembly 74 includes a light guide and a light source, both located entirely inside the camera assembly 70. The light guide 82 has a terminal end aiming at the image area 62 of the test channel 20 and a source end in communication with the light source. The light guides 82 are formed into shapes suitable for illuminating the image area 62. Light emitted by the light source is communicated to the terminal end of the light guide. Power for the light source is communicated into the camera assembly by the cable 78. The digital camera 70 is adapted to capture the image area 62 upon an activation signal. The activation signal is provided by the microprocessor 34 which has a programmed timing depending on the drying status provided by the first conductivity sensor or a humidity sensor mounted on a wall of the test channel, or by a manual operation depending on the visualization of saliva drying. The binary image data output from the image sensing CCD 76 is provided to the microprocessor 34, which includes a data acquisition component. The microprocessor generates pixel data representing the coordinates of the image pixels. The camera 70 is miniaturized for fitting into the drive head, whose size is designed for supporting the bristle elements. A CCD having diameter less than 5 mm is commercially available. Optionally, the camera assembly may utilize a CMOS photo diode array in place of the CCD type of photosensor array.

Figure 6A:
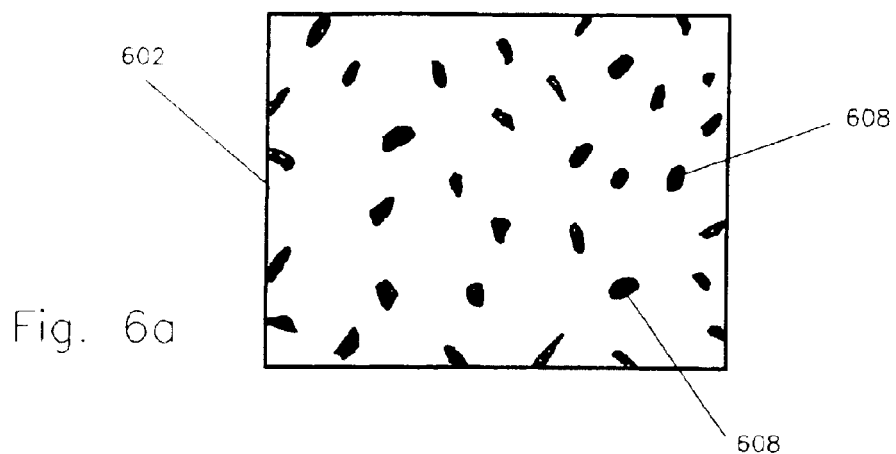
FIG. 6a is an illustration of a structureless random distribution of saliva dots in a dried saliva in a infertile time.
Figure 6B:
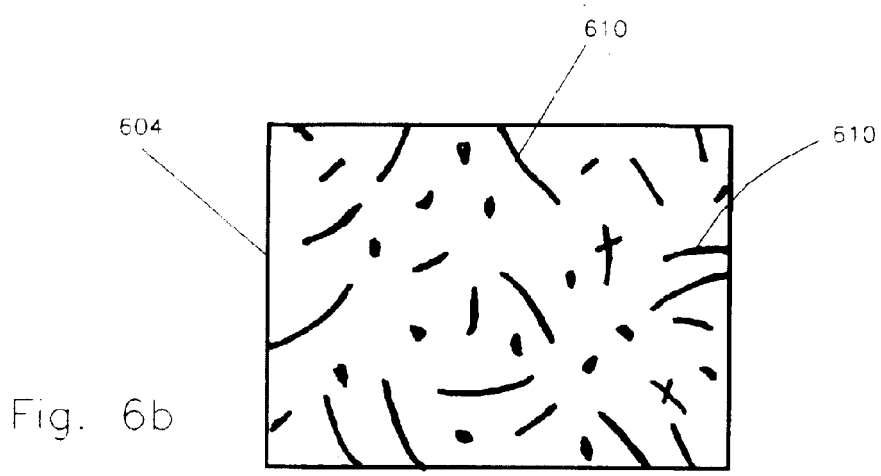
FIG. 6b is an illustration of the presence of connected saliva dots as line segments in a dried saliva near the time of ovulation.
Figure 6C:
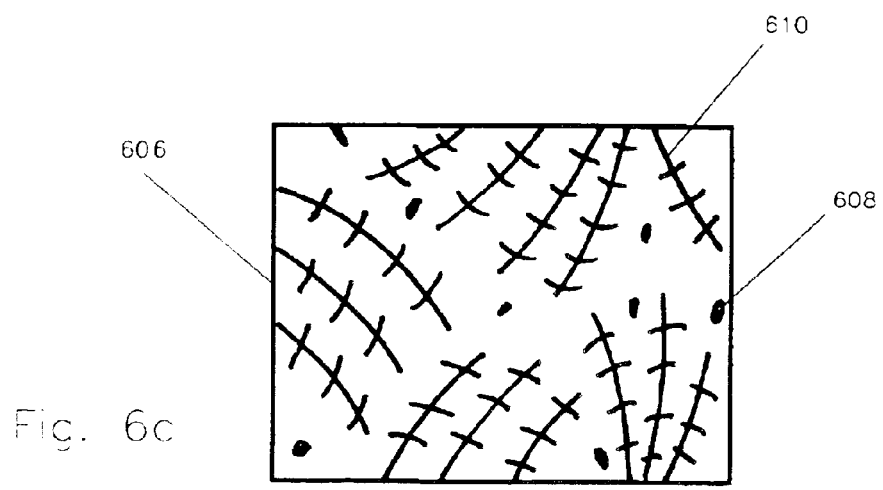
FIG. 6c is an illustration of the ferning pattern of structured line segments of saliva dots in a dried saliva at the time of ovulation.

The structure of a crystalline pattern shows characteristic features of line length, line width, line orientation and branching. Each of the features plays a role in the visual judgement of the degree of crystallization. FIGS. 6a, 6b and 6c show typical images 602, 604, 606 of a woman's dried saliva in infertile and fertile periods of a menstrual cycle. Physically the structured features as illustrated are related to the connectivity of saliva dots in the crystallization process. FIG. 6a illustrates a random distribution pattern 602 of unconnected saliva dots 608 during an infertile time when long-chain alcohol is at a constant level. FIG. 6b illustrates a partial crystalline pattern 604 with the presence of a significant degree of connected saliva dots or line segment 610 indicating the transition period. The increase of long-chain alcohol, particularly dodecanol near the time of ovulation results in the linking of the saliva dots that appear in line segments. The connectivity and the length of saliva dots increase to the maximum at the time of ovulation as shown in a nearly full crystalline pattern 606 in FIG. 6c. The presence and lengths of line segments can be correlated to the amount of the long-chain alcohol but in general the orientations of line segments, however, are affected by the distribution of saliva dots as well as the flow and handling of saliva sample in the liquid state on a test plate. In the present invention a single parameter, the characteristic line length, is directly measured for evaluating the connectivity of the saliva dots for representing the degree of crystallization. As will be shown later, the characteristic line width and branching are included in a statistical treatment in the calculation of the characteristic line length. The change of characteristic line length during a menstrual cycle is illustrated by a trend curve. The peak of the trend curve predicts the timing of ovulation.

Figure 7:
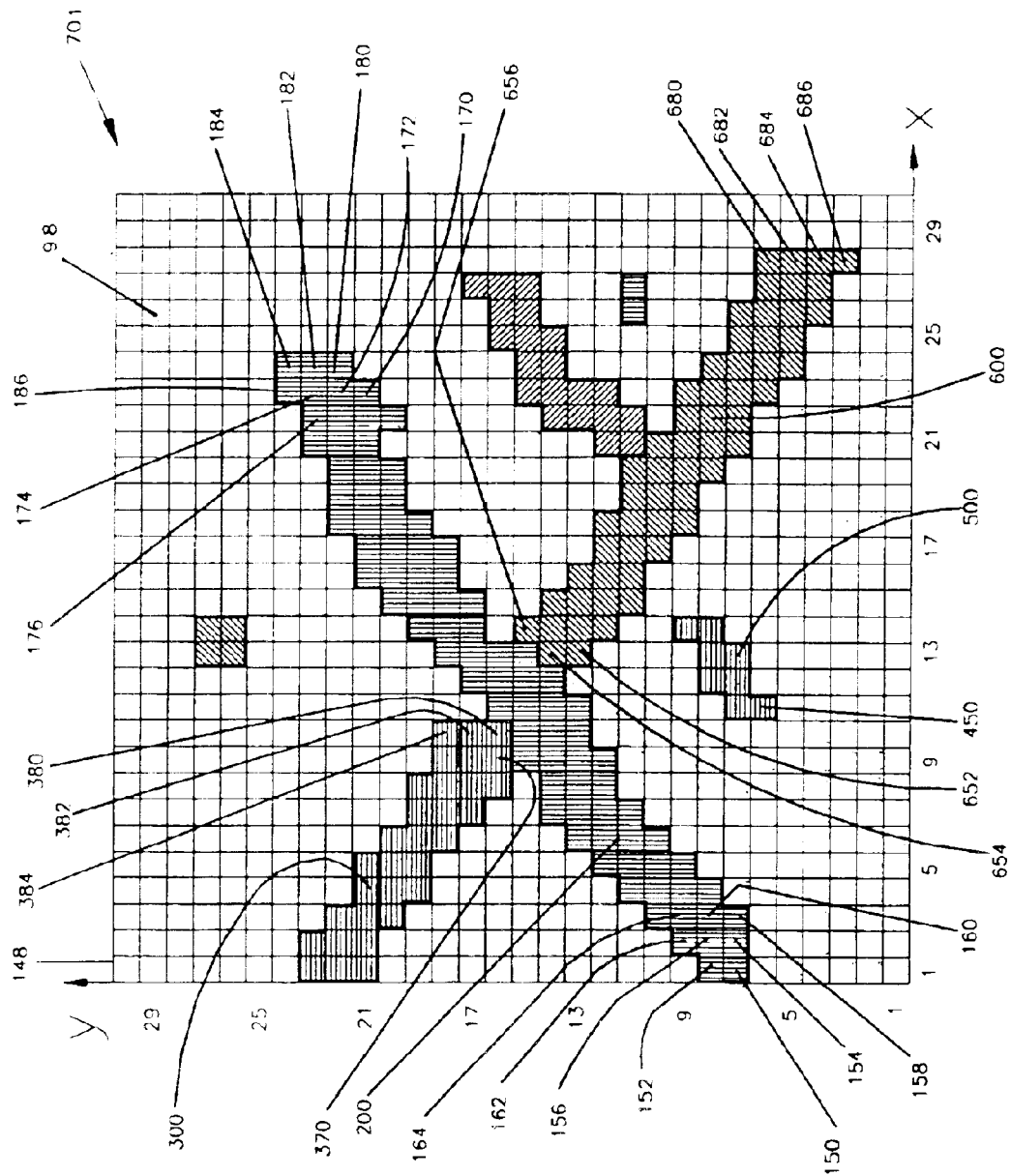
FIG. 7 is an illustration of line segments of a ferning pattern represented by connected dark pixels.

A method of automated image processing for the evaluation of a crystalline pattern includes the following steps: storing the test image pattern of the dried saliva sample, framing line segments, calculating the characteristic line length and the ferning index, as well as plotting trend curves. As shown in FIG. 7, the digitized image of targeted image area 701 captured by camera assembly 70 (shown in FIG. 2) contains a number of picture pixels 156 with each pixel having a three-dimensional information space. An image pixel of a line segment 200 has a two-dimensional array representing X and Y coordinates and the third dimension indicating the darkness of the pixel. The darkness of each pixel is represented by two ranges of optical density which are out of 256 gray-scale values between black and white. The first range of optical density, DB, includes the optical density of the background of transmissive window platen 60, which is presented in light pixels 98. The second range of optical density, DS, includes the optical density of the saliva dots image 156, which is preferably presented in dark pixels distinctively different from the background material of the transmissive window platen. The dark pixels generally reflecting the imaged saliva dots have a greater gray-scale value, and the light pixels generally have a much lesser gray-scale value. An optical pattern recognition program detects the two ranges of the optical density. By comparing the gray values of all the pixels, the optical pattern recognition program further obtains a binary quantification of the pixel patterns in "black" and "white" or in "zeros" and "ones" for identifying the light and the dark pixels of the saliva image respectively.

FIG. 7 describes the process of framing the line segments of an imaged crystalline pattern of a dried saliva. To identify a first line segment of a crystalline pattern, a vertical single pixel line is started for finding a head dark pixel. With the input of the stored pixel values of "zero" and "one", an image processing program proceeds to frame a first line segment by scanning from the most left end, X=1, of the field toward the right end of the field. It searches the stored pixel data vertically from bottom, Y=1, to top along the scan line for the optical density range $D_S$, which are dark pixels or "1" in the binary representation of saliva dots image to be included for identifying with the first line segment. The frame of the first line segment increases in size in the direction where the coverage area of dark pixels increases. The determination of the connectivity of the pixels is a known skill in the art. This operation is repeated until the final frame size is reached, in which the further increase of the frame size in any direction does not increase the coverage area of dark pixels. After framing the first line segment, the image processing program proceeds to establish the framing of the second and then subsequent line segments. Referring to FIG. 7, the framing process is detailed by the following steps:

1. Start from the first pixel column 148 at X=1 from the most left side of the image area 70 of the saliva sample.
2. Start from the bottom at Y=1 of the first pixel column 148 upward to find first head dark pixel 150.
3. After locating first head dark pixel 150, identify first tier of neighboring dark pixels 152 and 154 that are connected to first head dark pixel 150.
4. Extending from the first neighboring dark pixels, 152 and 154, find second tier neighboring dark pixels 158, 160, 162 and 164 that are connected to the first tier neighboring dark pixels.
5. By the same process, find end pixels which are Nth-tier neighboring dark pixels 180, 182, 184 and 186 that are connected to the (N−1)th-tier neighboring dark pixels 170, 172, 174 and 176, which are next to the end pixels. The connected pixels from the head pixels to the end pixels form first line segment 200.
6. The first line segment 200 includes all dark pixels that are connected forming the body and the edges of the line segment. Thus line segment 200 has a length and rough edges (uneven width along the length of the line segment) that forms an area coverage of connected dark pixels. Those dark pixels that form the first line segment 200 should be excluded from counting for other subsequent line segments.
7. Next, along the first pixel column 148 at X=1 upward, find the second head dark pixel if any. As shown in FIG. 7, the second head dark pixel is denoted by 302. By the same process for framing the first line segment 200, line segment 300 is identified and framed that it terminates at dark pixels 370, 380, 382 and 384.
8. Find the next head dark pixel if any on X=1 along Y-axis toward the top y=ym.
9. After framing all line segments starting from all head pixels on X=1, move to the second pixel column X=2. Start from the bottom Y=1 of the second pixel column upward to find the uncounted dark pixels that have not been included in the preceding framed line segments. Those uncounted dark pixels on column X=2 are new head dark pixels for the next line segments.
10. After locating the next head dark pixel 450, following the same process of identifying neighboring dark pixels to frame line segment 500.
11. Similarly, following on the same pixel column X=2, find the next head dark pixel if any, and by the same process frame the next line segment.
12. A head dark pixel may be next to a end dark pixel of a line segment. For example, line segment 600 spans from head dark pixels 652, 654 and 656 to terminal dark pixels 680, 682, 684 and 686.
13. In framing a line segment, use a line direction tangent from the preceding neighboring dark pixels to find next neighboring dark pixels.
14. A head dark pixel is a dark pixel that has not been included or counted in the preceding line segments.
15. A line segment may be linear or curvilinear. The algorithm for computing length of a curved line uses known mathematics formula.

As a summary, a matrix of line segments may be obtained for the whole image area. The matrix includes line segments with lengths from a single pixel to a long line segment across the image area. The total number of line segments is a sum of all the long and short line segments which also include unconnected dark pixels.

Figure 8:
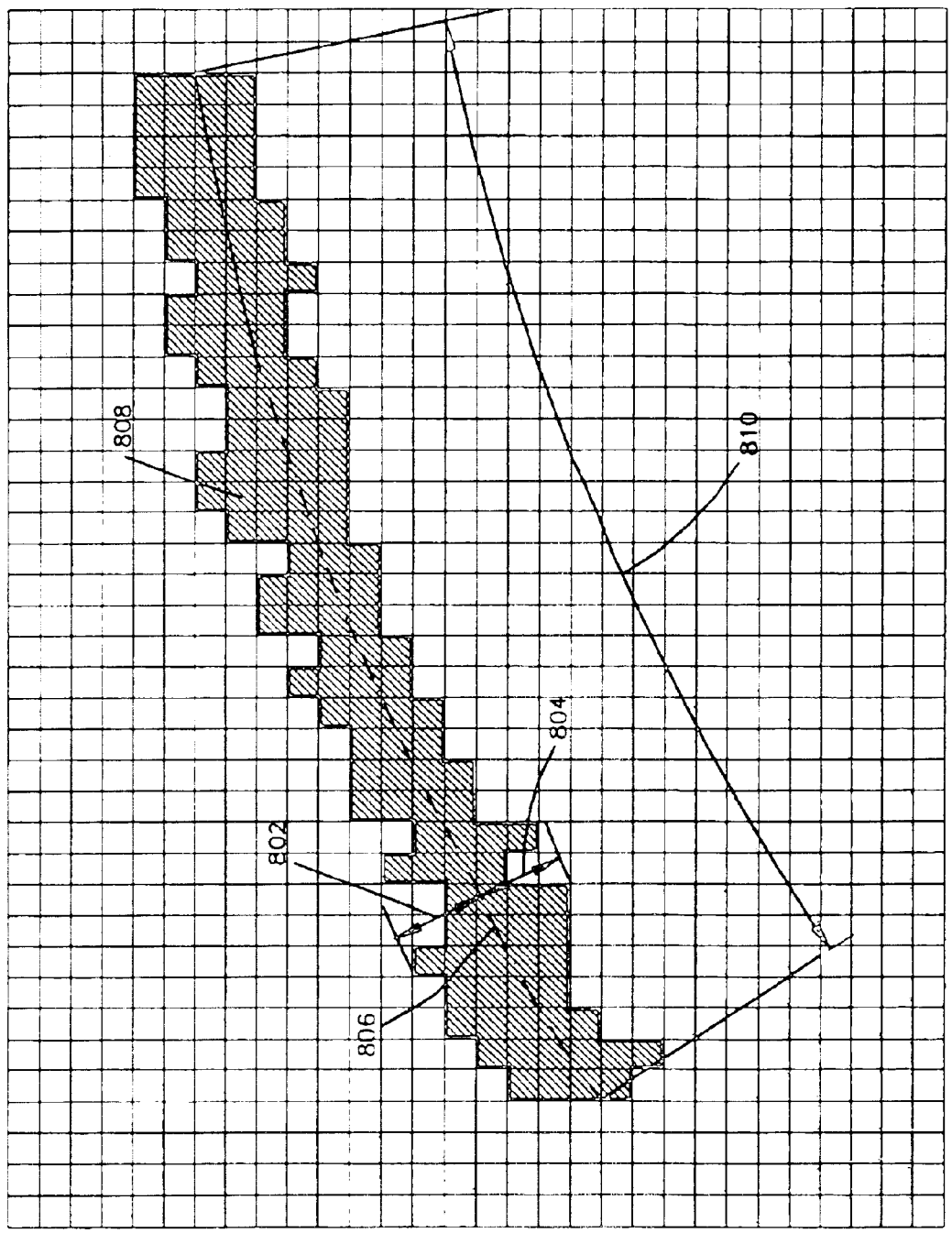
FIG. 8 is an illustration of the length and the mean width of a curved line segment.

Generally a framed line segment is non-linear and its width is non-uniform due to rugged edges. After framing a line segment, the mean width of a line segment is to be calculated. As shown in FIG. 8, local line width is the sum of height 802 above and height 804 below local centerline 806 of the line segment 808 where the local height 802 is the distance of an edge dark pixel normal to the intrinsic local centerline 806 of framed line segment 808. The centerline 806 of line segment 808 is determined by a statistical process that involves smoothening the edge profiles of the framed line segment. The edge smoothening technique is known in the art. Accordingly, the mean width of a line segment 808 is the average value of all the local widths integrated along the length 810 of the line segment 808. Such calculations are based on known geometric and statistic formulae. Consequently, the characteristic line width of the image area is the average value of mean widths of all line segments contained in the image area. The characteristic line width alone, however, is not a sensitive indicator for crystallization due to its insignificant change in crystalline patterns of dried saliva samples.

Based on a crystalline pattern of saliva dots, a characteristic line length can be calculated for representing the degree of crystallization of the dried saliva sample. Based on the connected dark pixels, by means of statistical treatment the characteristic line length can be calculated by the ratio of the sum of dark pixel area to the number of the line segment multiplying the characteristic line width as shown in the following first formula:

Characteristic Line Length=(Total Area Coverage)/(Number of Line Segments×Characteristic Line Width)

The total area coverage is the sum of all the dark pixel areas occupied by unconnected dark pixels and by the short and long line segments in a defined image area. The number of line segments and the characteristic line width are determined by the afore-described steps. For increasing the sensitivity of a trend curve of characteristic line length vs day, a threshold length as a truncation value may be used to exclude non-connected dark pixels or very short line segments from calculating the characteristic line length. The use of the threshold length for data analysis will be described later.

Figure 9:
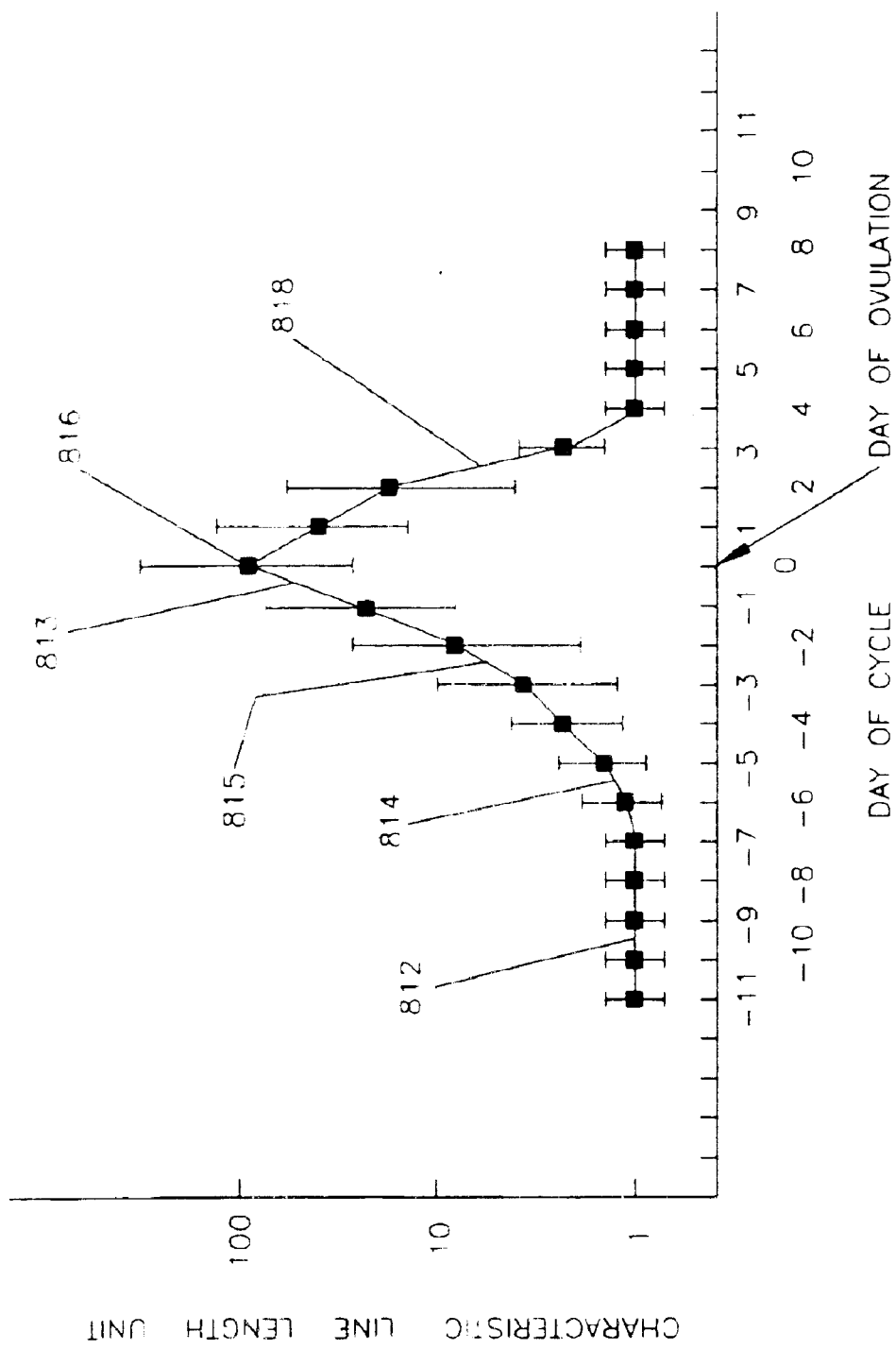
FIG. 9 is a display of trend curve of the characteristic line length near the time of ovulation.

FIG. 9 is a plot of trend curve 813 of characteristic line length vs day near the time of ovulation. The initial low level as indicated at flat portion 812 of characteristic line length indicates the random distribution of saliva dots 608 as shown in FIG. 6a. The initial increase portion as denoted 814 indicates the starting of crystallization which is about six or five days prior to ovulation. The crystalline pattern grows in the next few days as more saliva dots are connected into line segments 610 as shown in FIG. 6b. At this transition stage as indicated in rapid growth portion 815, ovulation is expected to happen in two to one day. Eventually the characteristic line length reaches a peak portion, denoted by 816, on the day of ovulation. At that time a very structured crystalline pattern appears as shown in FIG. 6c. Thereafter, the number of line segment starts to decrease as indicated by decline portion 818 of the trend curve, which returns to the same initial low level a indicated in 812 as in the infertile days.

Based on the mapping data of all the line segments in the image area, a ferning index can be calculated to provide a percentage number for indicating the degree of crystallization. In the present invention, the Ferning Index is defined by the following second formula:

Ferning Index=(Total Area Coverage−Truncated Area Coverage)/(Total Area Coverage)

Where the truncated area coverage is defined as the sum of dark pixel areas of line segments whose lengths are less than the threshold length. During an infertile time, for example eight days before ovulation, all line segments are unconnected saliva dots such that the truncated area coverage is the total area coverage of the saliva dots, accordingly, the Ferning Index is zero according to the above formula. On the fifth or the fourth day prior to ovulation, significant crystalline pattern starts to appear. The threshold length is a parameter value chosen to be equal to the characteristic line length of all the saliva dots connected and unconnected at the initial phase of crystallization computed according to the first formula. The initial phase of crystallization is when a significant number of short line segments appears among random saliva dots in the first two days of crystallization process. Based on the captured image of the dried saliva on the second day of crystallization a threshold characteristic line length is calculated. This threshold length is then used to determine the truncated area coverage of subsequent days for calculating the Ferning Index so as to establish a trend curve and to identify the peak of the curve. The peak of the Ferning Index curve indicates the day of ovulation. However, for predicting the day of ovulation, the rate of increase of the Ferning Index curve may indicate the impending ovulation in advance. The above definition of Ferning Index recognizes that not all saliva dots are connected at the peak of crystallization at the time of ovulation. Nevertheless, the percentage number of the Ferning Index indicates a degree of crystallization and provides a confidence level in the prediction of the ovulation day.

Figure 10:
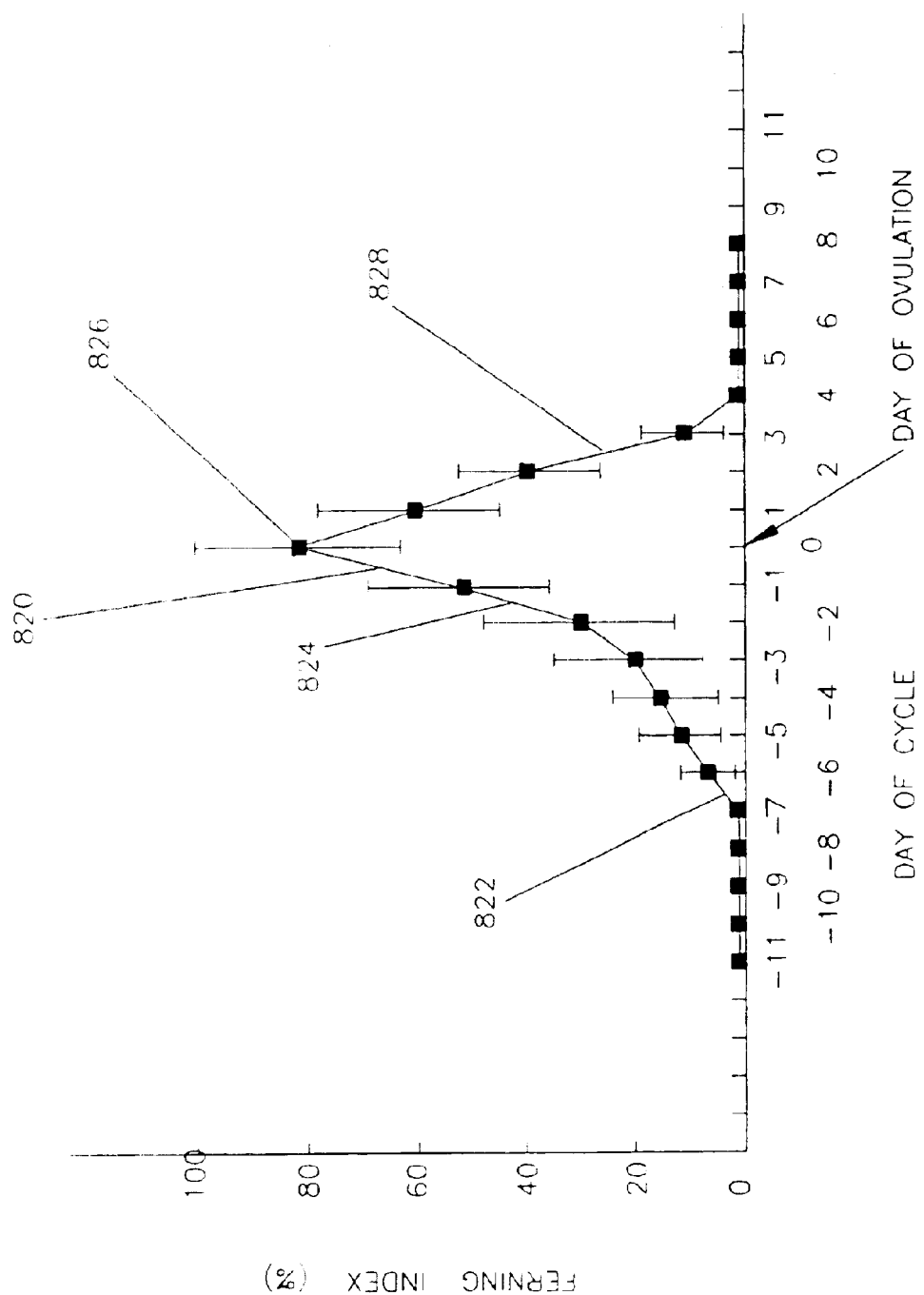
FIG. 10 is a display of a trend curve of the ferning index near the time of ovulation.

FIG. 10 shows trend curve 820 of the Ferning Index corresponding to the characteristic line length shown in FIG. 9. The Ferning Index is at zero on infertile days prior to the initial stage of crystallization due to the use of the threshold length for excluding the coverage areas of the randomly distributed saliva dots. Similarly, rise portion 822, growth portion 824, peak portion 826 and decline portion 828 of trend curve 820 are corresponding to their counterparts, 814, 815, 816, and 818, respectively, in trend curve 813 of the characteristic line length as shown in FIG. 9.

Figure 11:
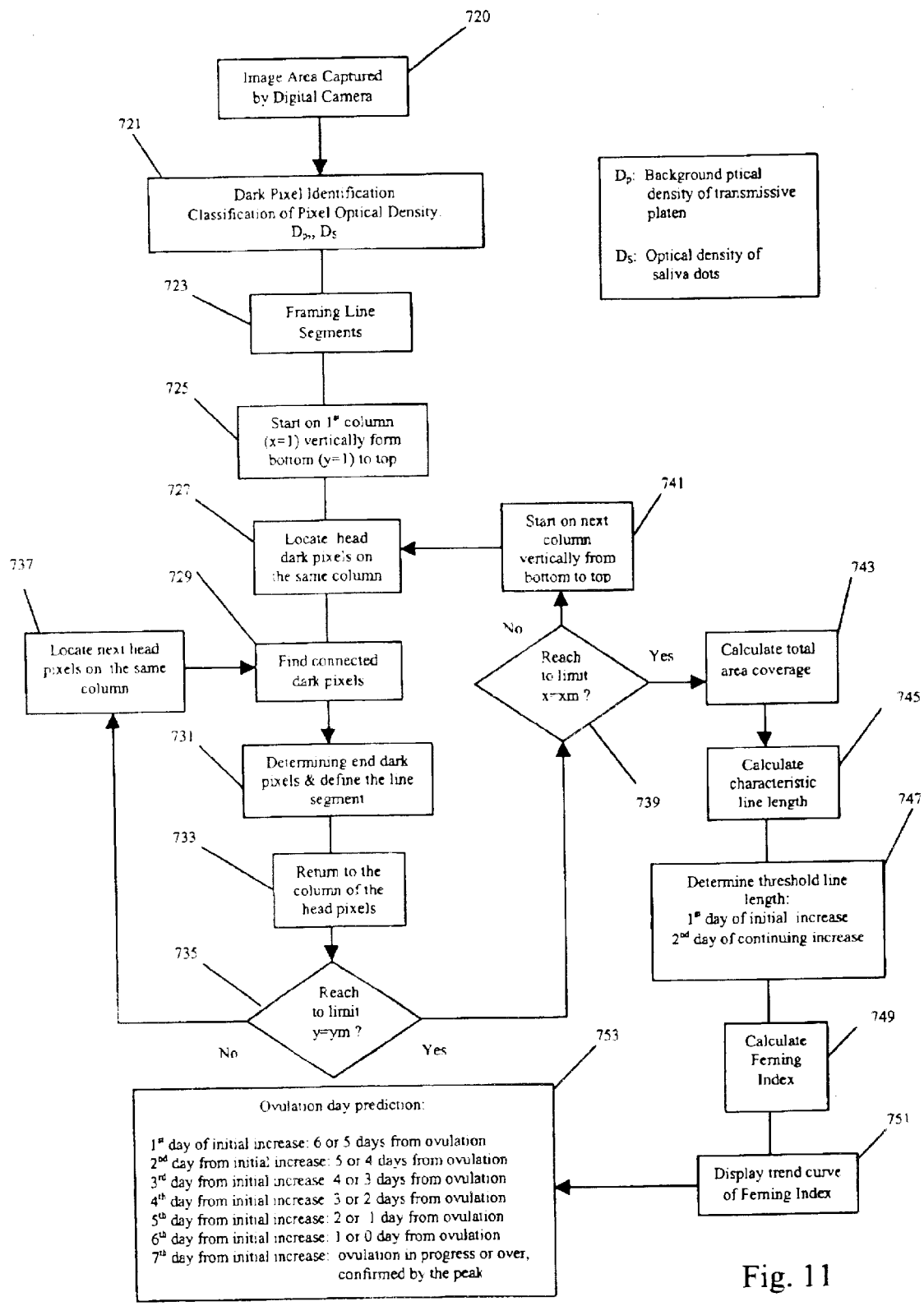
FIG. 11 is a flow chart of image processing and computational steps for determining the characteristic line length and the ferning index.

As a summary, referring to FIG. 11, the process of calculating saliva Ferning Index and the prediction of ovulation comprises: (1) step 720 of capturing image area of a dried saliva sample by camera; (2) process 723 of framing line segments including steps 721, 725 and 727 of identifying dark pixels, and steps 729, 731 of finding connected and end dark pixels of a line segment; (3) steps 733, 735 and 737 of finding new head dark pixels and repeating the same process till reaching the top of the same column; (4) steps 741, 737 and 739 of finding head dark pixels on the next column and repeating the same process till reaching the end of the last column; (5) steps 743 and 745 of calculating total area coverage and characteristic line length; (6) steps 749 and 747 of determining threshold line length, number of line segments and calculating the Ferning Index; and (7) step 753 of displaying the trend curves and prediction of the ovulation day.

Figure 12:
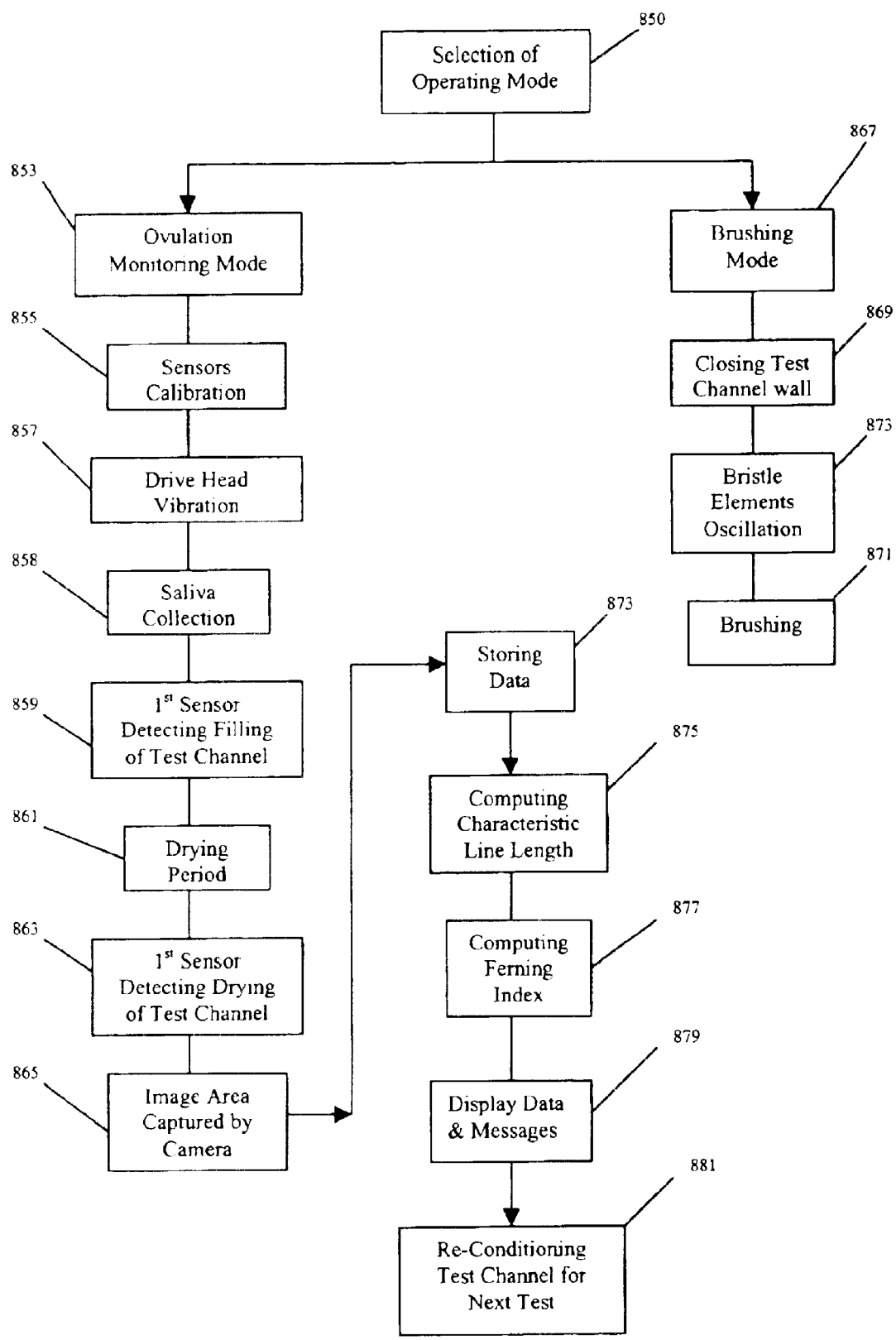
FIG. 12 is a flow chart of operation of the ovulation-monitoring electrical toothbrush.

A flow chart 850 for the operation of an ovulation-monitoring electrical toothbrush of the present invention is shown in FIG. 12. An ovulation-monitoring electrical toothbrush has two operating modes; brushing mode 867 and ovulation-monitoring mode 853. When the ovulation-monitoring mode is selected, step 855 of calibrating first and second sensors is initiated and then followed by vibration step 857 of the drive head. Step 858 of collecting saliva sample is achieved by immersing the test channel of the vibrating drivehead in the saliva pool under the tongue. Filling stage 859 of test channel is detected by the first sensor. Then the test channel undergoes a drying period 861, which is monitored by intermittent conductivity measurements by the first sensor through programmed time intervals for comparing with a predetermined threshold line length for determining the drying state 863 of the test channel having the saliva sample. The time interval of measurements is enabled by using a clock in communication with the microprocessor.

On FIG. 12, after confirming the drying of the saliva sample, image 865 of dried saliva is captured by the digital camera situated inside the drive head. Stored image data 873 of saliva dots are distinguished between light and dark pixels. Based on the binary information of unconnected saliva dots and connected line segments, the computations of characteristic line length 875 and Ferning Index 877 of the imaged area of dried saliva sample are performed. Repeated daily measurements of crystalline patterns and computations of Ferning Index enable plotting of a trend curve for display 879 and providing prediction of impending ovulation. After each saliva testing for ovulation, re-conditioning 881 of the test channel by cleaning is required for next testing.

On the other hand, when brushing mode 867 is selected, the microprocessor initiates step 869 of providing an acoustic or visual signal to the user to close the upper channel wall. A closed test channel can prevent contamination of the test channel from the brushing. Then subsequent step 873 of bristle oscillation is manually activated by the user for brushing 871. The test channel can remain closed until the ovulation monitoring mode is selected. The brushing mode may immediately follow the ovulation monitoring mode if the test channel is closed for protecting the saliva sample inside from contamination as described previously.

Figures 13A, 13B:
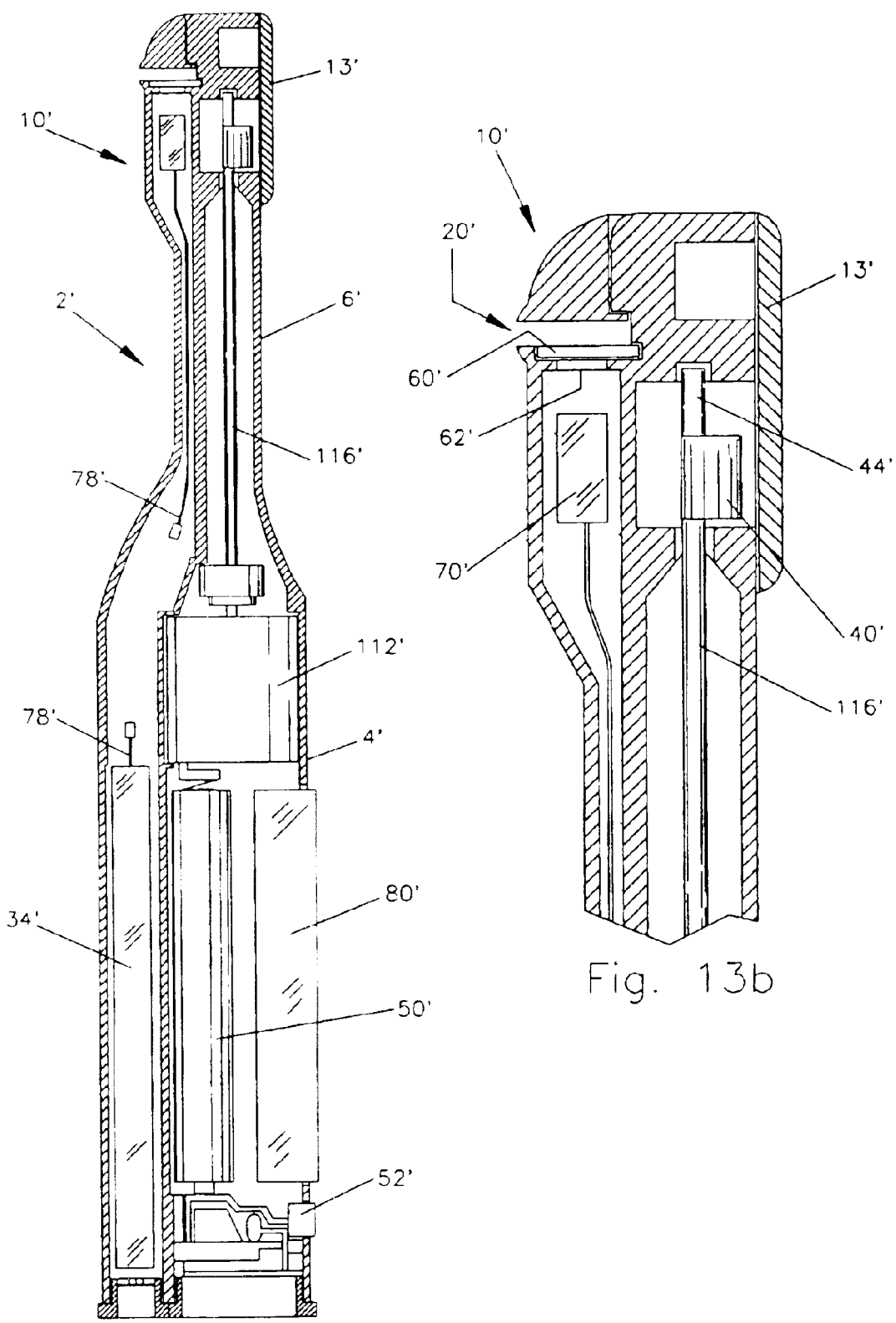

The methods of saliva stimulation, collection and the configuration of the test channel are applicable to a handheld oral device with or without bristle elements. An ovulation-monitoring oral device may be functionally similarly to the toothbrush shown and described in FIG. 1*a* except that the test channel is housed in a test head without having bristle elements for brushing teeth. FIG. 13*a* shows an ovulation-monitoring oral device 2' having handle 4' and test head 10' connected by neck 6'. Motor 112' and batteries 50' are positioned within handle 4'. Switch 52' extends through an opening in the base of the handle for activating the operation of the oral device. Drive shaft 116', having a central longitudinal axis with first end engaged with the motor and second end mounted with biased wheel 40' for imparting the vibration motion when the motor is turn on. Test head 10' has test channel 20' for collecting a saliva sample and camera assembly 70' for capturing image picture of a dried saliva through optically transmissive window platen 60' on its lower wall as shown in partially enlarged view in FIG. 13*b*. Microprocessor 34' which is in communication with camera assembly 70' through cable 78' is for the control of the electrical components and the calculations of characteristic line length and the Ferning Index. In addition, display 80' is for the display of trend curve of Ferning Index as described previously. As a multiple function oral device, replaceable platform 13' may be attached with a gum massaging element and mounted on test head 10'.

Figures 14A, 14B:
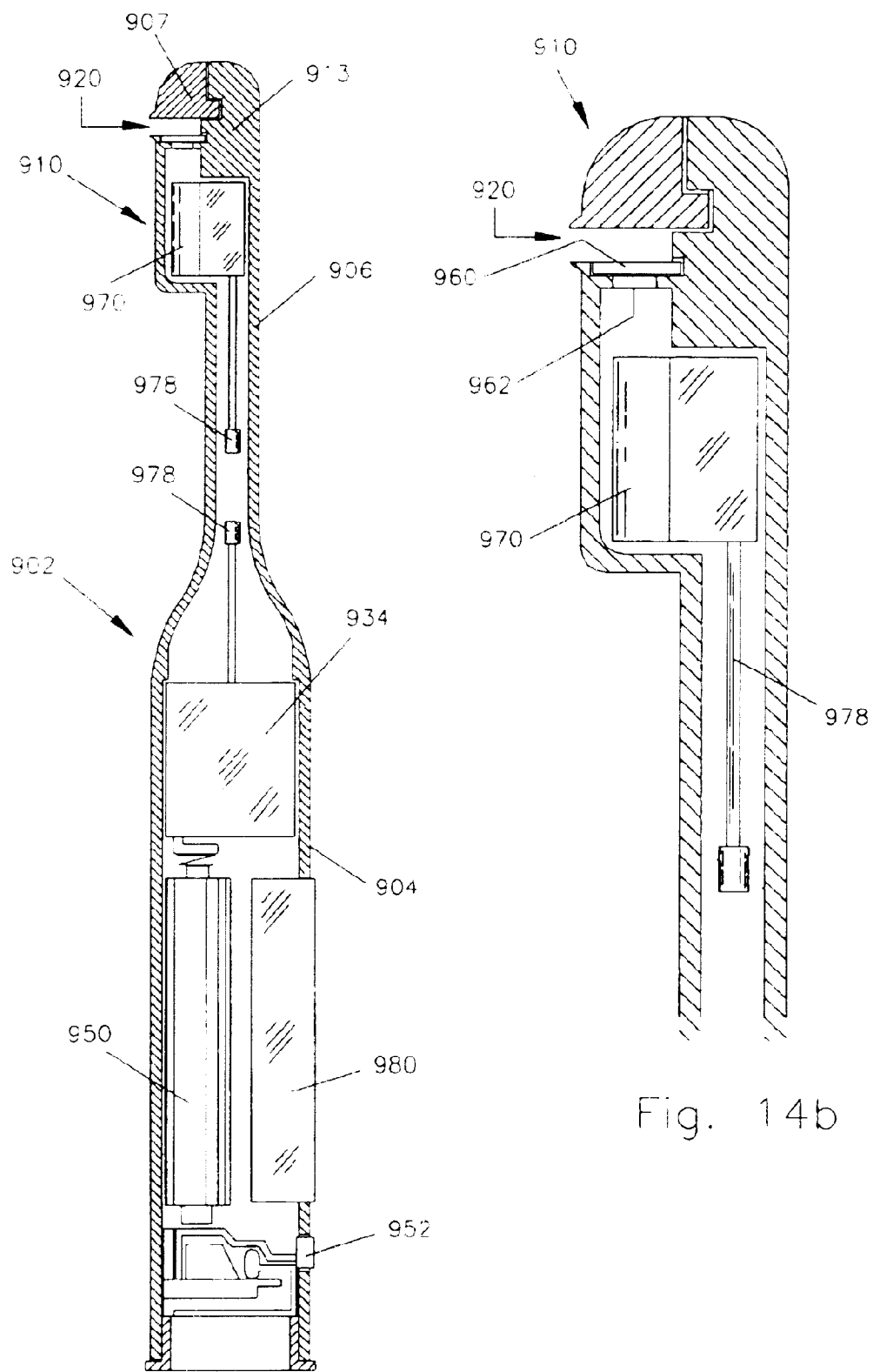

Optionally, an ovulation-monitoring oral device of the present invention may be further simplified without having the vibration function as described above. For using such a simplified oral device, the vibration function for stimulating saliva secretion can be accomplished by using of a separate electrical toothbrush by placing its oscillating brush head under the tongue. FIG. 14*a* shows an ovulation-monitoring oral device 902 having handle 904 and test head 910 connected by neck 906. Microprocessor 934, batteries 950 and display 980 are included in handle 904. Switch 952 extends through an opening in the base of the handle for activating the operation of the oral device. Test head 910 has test channel 920 with upper wall 907 for collecting a saliva sample and camera assembly 970 for capturing image picture of a dried saliva through optically transmissive window platen 960 on its lower wall as shown in partially enlarged view in FIG. 14*b*. Microprocessor 934, being in communication with camera assembly 970 through cable 978, is for the control of the electrical components and the calculations of characteristic line length and the Ferning Index. Additionally display 980 is for the display of trend curve of Ferning Index. Similarly, for an added function, replaceable platform 913 may be attached with a tongue scrapper and mounted on drive head 910.

The present invention has been described in detail with reference to preferred embodiments thereof. However, variations and modifications can be implemented within the spirit and scope of this invention. The oral device of the present invention may be without having the upper channel wall and a saliva sample is placed on top of a transmissive window platen for image taken by a camera, which is situated underneath the window platen, for image analysis for computing the characteristic line length and the Ferning Index for the prediction of ovulation. The second sensor in the test channel may be a proximity sensor for detecting closed or open position of the upper channel wall or optionally be a heating element for the drying of liquid saliva. Instead of processing the image data by the internal microprocessor, the digital image signal input from the digital camera can be transmitted by wireless signal transmitting circuit to a computer which is loaded with an imaging processing software for analysis. Furthermore, the image of a dried saliva may be optionally transmitted by optical fibers to a digital camera positioned external to the handle of an oral device as described by the present invention. The use of optical fibers for transmitting optical image is well known in the art.

I claim:

1. An image processing system for predicting ovulation of a female comprising:
   a. means for providing a digital image of a dried saliva sample obtained from the female;
   b. image processing means for calculating characteristic line length of all saliva dots in an image area of the digital image of a dried saliva sample; and
   c. means for predicting ovulation based on an increase of said characteristic line length.

2. An image processing system for predicting ovulation of a female of claim 1, wherein said image processing means comprises means for calculating a Ferning Index, wherein said Ferning Index is based on a percentage of area coverage of connected saliva dots in the digital image whose line lengths exceed a threshold line length, wherein said threshold line length is the characteristic line length at the initial stage of an increase of crystallization of saliva samples taken prior to the ovulation day.

3. An image processing system for predicting ovulation of a female of claim 1, wherein the increase of said characteristic line length is displayed as a trend curve.

4. An image processing system for predicting ovulation of a female of claim 1, wherein said image processing means comprises:
   a. means for digitizing the digital image of the dried saliva sample by distinguishing saliva dots with dark pixels and background material as light pixels; and
   b. means for defining and framing line segments of saliva dots.

5. An image processing system for predicting ovulation of a female of claim 4, wherein said image processing means further comprises means for excluding dark pixels from repeated counting in framing a new line segment.

6. An image processing system for predicting ovulation of a female of claim 5, wherein said image processing means further comprises means for calculating a Ferning Index, wherein said Ferning Index is based on a percentage of area coverage of connected saliva dots in the digital image whose line lengths exceed a threshold line length.

7. An image processing system for predicting ovulation of a female of claim 1, wherein said means for providing a digital image of a saliva sample comprises:
   a. a handle containing a sample platen and a digital camera; and
   b. means for positioning the dried saliva sample on the sample platen for capturing a digital image with the digital camera.

8. An image processing system for predicting ovulation of a female of claim 7, wherein the handle includes a vibratory test head having a test channel defined by channel walls for inducing capillary flow and holding the saliva sample.

9. An image processing system for predicting ovulation of a female of claim 8, wherein said test head includes a sensor for detecting drying of said saliva sample.

10. An image processing system for predicting ovulation of a female of claim 9, wherein said sensor includes an electrode and a counter electrode, wherein said electrode and said counter electrode form a gap for filling with said saliva sample.

11. An image processing system for predicting ovulation of a female of claim 8, wherein said test channel comprises an upper wall, a lower wall and a base, and said upper wall and said lower wall form a flow channel which is capable of filling and retaining a saliva sample by capillary force.

12. An image processing system for predicting ovulation of a female of claim 11, wherein the upper wall is detachable from the test channel.

13. An image processing system for predicting ovulation of a female of claim 8, wherein the vibratory test head includes a driving means for imparting a vibrating motion to the test head.

14. An image processing system for predicting ovulation of a female of claim 13, further including a bristle element attached to the test head.

15. An image processing system for predicting ovulation of a female of claim 7, where the image processing means includes a microprocessor in communication with the digital camera.

16. An image processing system for predicting ovulation of a female of claim 15 including a display for displaying outputs of said image processing means.

* * * * *